United States Patent
Tranchant et al.

(10) Patent No.: US 7,780,350 B2
(45) Date of Patent: Aug. 24, 2010

(54) POSITIONING ADJUSTMENT OF A MOBILE RADIOLOGY FACILITY

(76) Inventors: Pierre Tranchant, 70 rue Désiré Richebois, Fontenay Sous Bois (FR) 94120; Sergio Serafini, 12D Avenue Frédéric le Play, Marseille (FR) 13009

( * ) Notice: Subject to any disclaimer, the term of this patent is extended or adjusted under 35 U.S.C. 154(b) by 0 days.

(21) Appl. No.: 12/282,256

(22) PCT Filed: Apr. 3, 2007

(86) PCT No.: PCT/FR2007/000565

§ 371 (c)(1),
(2), (4) Date: Sep. 9, 2008

(87) PCT Pub. No.: WO2007/118990

PCT Pub. Date: Oct. 25, 2007

(65) Prior Publication Data

US 2009/0060145 A1    Mar. 5, 2009

(30) Foreign Application Priority Data

Apr. 4, 2006  (FR) ................................... 06 02939

(51) Int. Cl.
*A61B 6/08* (2006.01)
(52) U.S. Cl. ........................................ 378/205; 378/38
(58) Field of Classification Search ............. 378/38–40, 378/205, 207
See application file for complete search history.

(56) References Cited

U.S. PATENT DOCUMENTS

| 4,223,228 A | 9/1980 | Kaplan |
| 4,792,228 A | 12/1988 | Haffner |
| 4,796,200 A | 1/1989 | Pryor |
| 5,463,669 A * | 10/1995 | Kaplan ........................ 378/205 |
| 7,319,396 B2 | 1/2008 | Homanfar et al. ......... 340/572.1 |
| 2005/0013412 A1 | 1/2005 | Calderwood et al. |

FOREIGN PATENT DOCUMENTS

| EP | 0506559 A1 | 9/1992 |
| WO | 2006008338 A1 | 1/2006 |
| WO | 2006023674 A1 | 3/2006 |

* cited by examiner

*Primary Examiner*—Courtney Thomas
(74) *Attorney, Agent, or Firm*—Volpe and Koenig PC (57) ABSTRACT

The invention concerns a device for detecting a faulty positioning between a first element and a second element comprising an electromagnetic wave emitting unit designed to be secured to the first element and an electromagnetic wave receiving and processing unit designed to be secured to the second element. The latter unit co-operates with the electromagnetic wave emitting unit to detect a faulty positioning of the first element relative to the second element. When used for a mobile radiology facility, the first element is, for example, an X-ray generator, and second element is, for example, a radiological image sensor.

19 Claims, 4 Drawing Sheets

EMISSION    RECEPTION

EMISSION    RECEPTION

POSITIONING ADJUSTMENT OF A MOBILE RADIOLOGY FACILITY

The present invention generally relates to mobile imaging, especially by X-rays, and more particularly to the positioning adjustment of a mobile radiology apparatus. It has applications, in particular, in digital dental radiology.

Figure 1:
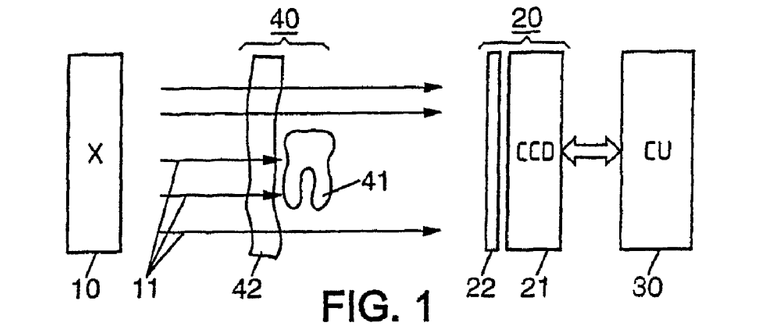
FIG. 1, already analyzed, is a diagram illustrating the principle of digital dental radiology.

With reference to FIG. 1, a mobile imaging facility, for example a digital dental radiology facility, comprises a source 10 of radiation (for example, X-rays), an image sensor 20 and a control unit 30. The sensor 20 may comprise a digital detector 21 of the CCD (Charge Coupled Device) type, associated with a scintillator 22. The detector 21 is sensitive to photons with a wavelength in the visible region. The scintillator 22 plays the role of a wavelength converter by receiving X-rays at the input and by delivering photons of visible light at the output. The control unit 30 is coupled to the sensor 20 to control the operation of the facility.

In operation an object 40 is placed between the source 10 and the sensor 20. In the application example envisioned here, the object 40 comprises elements exhibiting a certain opacity to X-rays, such as a tooth 41 of a patient, and elements that are transparent or of low opacity to X-rays such as the cheek 42 of the patient. The image obtained on the digital sensor 20 contains the image of the target, namely the tooth 41.

In the case of a mobile facility, such as a dental radiology facility, the X-ray source 10 and the digital sensor 20 are not joined to each other. In fact, the sensor 20 is designed to be placed in the mouth of the patient against the targeted tooth, and the user (in general the dental practitioner or his/her assistant) must hold the source 10 in front of the sensitive surface of the sensor 20 and find the right position of the source 10 relative to the sensor 20, in which the targeted tooth is in addition situated between the source and the sensor.

To solve this problem a mechanical device called a sensor holder has been proposed.

Figure 2:
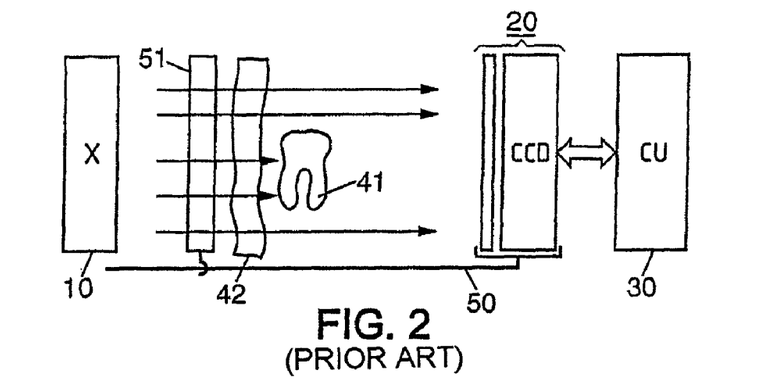
FIG. 2, also already analyzed, is a diagram that illustrates a solution, known in the prior art by the name of a sensor holder, for solving the problem of the relative positioning of the radiation source and the sensor in the context of digital dental radiology.

With reference to FIG. 2, a sensor holder 50 comprises a support rod joined to the sensor 20 and along which a ring 51 is able to slide. In operation the sensor 20 is introduced into the mouth of the patient on the side opposite the inner side of the cheek of the patient and the ring 51 is brought against the outer side of the cheek of the patient. The user then puts the X-ray source 10 against the ring 51, which allows the X-ray source to be positioned better in front of the sensor, and also the direction of the X-rays to be aligned better along the axis perpendicular to the sensitive surface of the sensor 20.

The use of such a sensor holder is, however, time-consuming and tedious. In addition, the elements for fastening the sensor to the sensor holder are visible on the radiograph and it is not always possible to use them.

In order to solve these problems, the present invention proposes, according to a first aspect, a device for detecting incorrect positioning between a first element and a second element which comprises:

a unit for emitting electromagnetic waves suited to pass through human tissues, the emission unit being designed to be joined to the first element; and a unit for receiving electromagnetic waves and for digital processing designed to be joined to the second element, and cooperating with the electromagnetic wave emission unit to detect incorrect positioning of the first element relative to the second element.

Advantageously, such a device can be adapted to an existing mobile radiology facility. The first element is then the radiation source and the second element is the image sensor. The application of the device is, however, not limited to this example, the device being able to be used to help in positioning all types of elements.

The expression "suited to pass through human tissues", in relation to electromagnetic waves, is of course understood to be in a manner not damaging for the physical integrity and the health of the subject. Such electromagnetic waves are, for example, radio waves (produced by high-frequency electrical currents) of appropriate power. For example, the frequency of the electromagnetic waves may be less than 100 MHz, and more particularly included in the band [10 kHz-100 MHz].

According to a second aspect, the invention also proposes a mobile imaging facility of the type comprising:

a radiation source; and an image sensor, having a surface sensitive to the radiation generated by the radiation source and not joined to the radiation source.

The facility furthermore comprises a device for detecting incorrect positioning according to the first aspect above, of which:

the electromagnetic wave emission unit is joined to the radiation source; and the unit for receiving electromagnetic waves and for digital processing is joined to the image sensor.

According to a third aspect, the invention also proposes a mobile imaging facility of the above type, but in which the facility furthermore comprises a device for detecting incorrect positioning according to the first aspect above, of which:

the electromagnetic wave emission unit is joined to the image sensor; and the unit for receiving electromagnetic waves and for digital processing is joined to the radiation source.

The incorrect positioning may be indicated to the user in any suitable manner. The user can then change the position of the source and/or sensor. As a variant, the information about the incorrect positioning may be used to change the position of the radiation source automatically via a position control servo system. The invention therefore offers an advantageous alternative to the device called a "sensor holder".

In embodiments in which the number of electromagnetic emitters in the electromagnetic wave emission unit is at least equal to 4, the electromagnetic wave reception unit is configured, in addition, to detect an angle between a plane of the electromagnetic wave emission unit and a plane of the electromagnetic wave reception unit. This angle corresponds to the error in angular position (also called the parallax error) between the radiation source and the sensor.

This enables the user to correct the angle of incidence of the emitted radiation (i.e. of X-rays) with the direction orthogonal to the place of the sensor manually to reduce the parallax error. Hence, the radiological image that is obtained is less distorted, so that the real proportions of the radiographed target are better preserved.

In some embodiments, the electromagnetic wave reception unit comprises a number M of electromagnetic receivers located in the same plane and in respective positions that are nonsymmetrical relative to a first axis and/or a second axis in said plane, where M is an integer greater than or equal to 2. Furthermore, the electromagnetic wave reception unit is configured, in addition, to determine by signal processing the signals coming from the various electromagnetic emitters for each of the M electromagnetic receivers and to deduce from this a rotation of said plane relative to said first axis and/or said second axis respectively.

These embodiments enable the orientation (i.e. the angular position) of the image sensor in its own plane to be detected, and hence in particular automatic determination of whether the user produces a radiograph of the upper or lower jaw, from the right or left side of the mouth.

Other features and advantages of the invention will become apparent on reading the description to follow. This is purely illustrative and should be read with regard to the appended drawings in which.

In what follows and in the figures the same elements have the same reference signs. The invention is described in its non-limiting application to a mobile digital radiology facility, such as a digital dental radiology facility. A mobile radiology facility is understood to mean a facility in which the radiation source and/or the image sensor are not joined to each other. A digital facility is understood to mean a facility in which the image acquisition process is at least partly carried out by digital means.

Functional Description of the Facility

Figure 3:
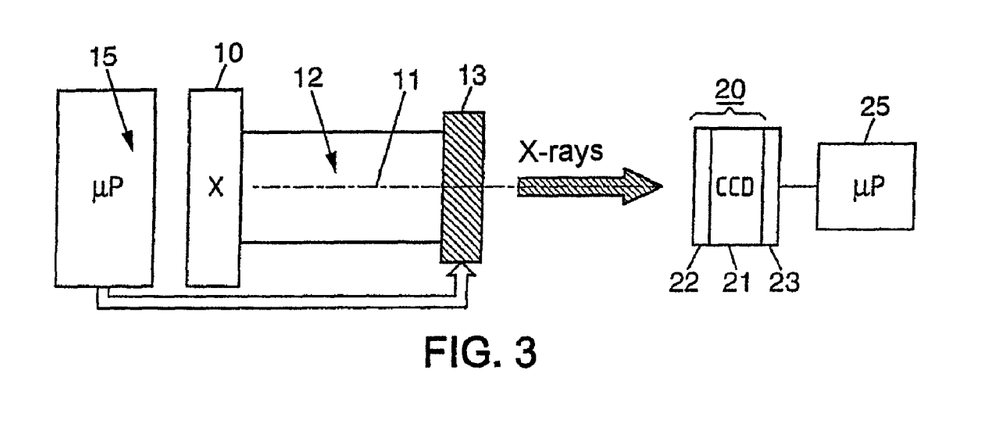
FIG. 3 and FIG. 4 are diagrams illustrating an embodiment and the operational principle of a facility that is the subject of the present invention.
Figure 4:
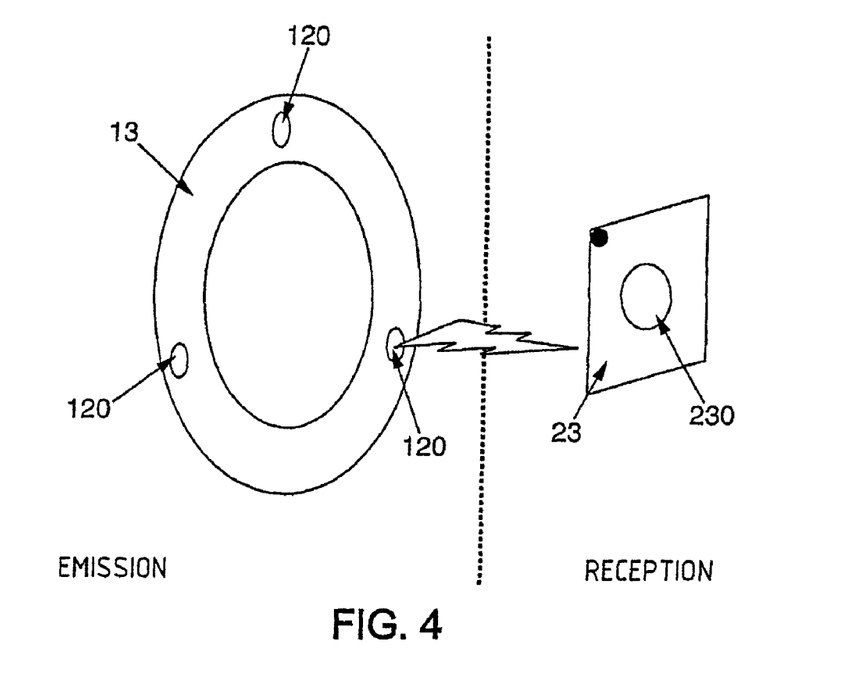

With reference to FIG. 3 and FIG. 4, a digital radiology facility according to the embodiments of the invention comprises a radiation source 10, such as an X-ray generator. The gun 12 of the generator is a cylinder which has the function of shaping the X-ray beam generated, such that it has the form, for example, of a cone with a very small opening, i.e. of approximately constant diameter, and equal to 60 mm for example. The main axis of the gun 12 corresponds to the axis of incidence 11 of the X-rays generated.

The facility also comprises a digital image sensor 20. It may comprise a CCD 22 associated with a scintillator 21 (which, in operation, is positioned alongside the CCD which is directed toward the X-ray source). The CCD image sensor is, for example, of size 2, i.e. its sensitive surface corresponds to a rectangle of diameter equal to 48 mm. The image sensor is coupled to a control and exploitation unit, which produces the actual radiological image.

Dimensions other than those indicated above are of course conceivable, but these are typical of an application to digital dental radiology.

To assist the correct positioning of the radiation source 10 and of the image sensor 20, the facility furthermore includes an electromagnetic wave emission unit 13 that can be joined to the source 10 and an electromagnetic wave reception unit that can be joined to the image sensor 20, one cooperating with the other. These elements form a device that enables incorrect positioning of the radiation source 10 relative to the image sensor 20 to be detected.

The device is designed to indicate any error in positioning to the user. This error can then be manually corrected by the practitioner or via a robotic control device. To this end, the source 10 can be mounted on a mechanical system or a pantograph in a stable but movable and adjustable manner. As a variant, the error in positioning is provided as the input to a servo control device that automatically positions the X-ray source relative to the image sensor.

Due to medical standards and ease of integration, it is advantageous to put the electromagnetic wave receiver and not the electromagnetic wave emitter at the level of the image sensor. This is because it is preferable not to emit power at the sensor which, in operation, in placed in the mouth of the patient. The risk of possibly giving off heat likely to disturb or frighten the patient is avoided or at least substantially reduced. The disturbance of radiation measurements by the image sensor is also reduced. Moreover, this assists in complying with electromagnetic compatibility standards (EMI, Electromagnetic Interference) which are very strict for this class of apparatus.

On the emission side, the device for detecting incorrect positioning comprises an electromagnetic wave emission unit which, in the operational situation, is joined to the radiation source 10. This emission unit is controlled by a unit 15. The unit 15 comprises, for example, a microprocessor controlled by software. The emission unit also comprises a set of at least 3 controlled electromagnetic wave generators 120, such as solenoids. The solenoids are, for example, located in the same plane, which is perpendicular to the incident axis 11 of the X-ray beam. They are arranged, for example, on a toric support 13, the inner diameter of which is designed so that it fixes to the bottom of the gun of the generator 10. With this arrangement, the plane of the support 13 corresponds to the plane of the end of the gun 12 of the generator 10.

As can be seen in FIG. 4, the solenoids 120 are preferably distributed equidistantly (i.e. in equally distributed angular positions) along the rim formed by the main plane of the support 13. This arrangement allows the processing carried out on the reception side to be simplified. In the figure there are hence 3 solenoids, angularly spaced two at a time by 120 degrees.

These solenoids 120 each emit a directional magnetic field with a certain recurrence. To this end, they are excited by a control system managed by the control unit 15. More particularly, the unit 15 takes responsibility for modulating this field according to a frame having a binary pattern specific to each of the emission solenoids. This enables the reception unit, by signal processing, to identify (i.e. to determine and to separate) the signals coming from different emission solenoids.

On the reception side, the device for detecting incorrect positioning comprises at least one reception solenoid 230 which, in the operational situation, is joined to the image sensor 20. This solenoid is located, for example, on a plate 23 arranged behind the sensor, i.e. on the side opposite the sensitive surface of the sensor, i.e. also on the side of the CCD 22 which is opposite the scintillator 21, or else on the side of the sensor 20 which, in operation, is opposite the source 10.

The electromagnetic wave reception unit also comprises processing means, such as an exploitation unit 25. The unit 25 contains, for example, a microprocessor and is controlled by software. It can advantageously be combined with the control and exploitation unit of the digital image sensor 20, these elements being, for example, realized in the form of a computer, for example a conventional personal computer.

Just as illustrated in FIG. 4, the reception solenoid 230 detects the magnetic field coming from an emitter solenoid.

The signal thus detected is electronically conditioned then digitized to be analyzed by signal processing at the unit 25.

General Operational Principle

The intensity and the phase of the electromagnetic fields depend on the distance and the angle at which they are measured, relative to their point of emission, i.e. the location of the emission solenoids that generate them.

The electromagnetic waves generated are suited to pass through human tissues, in a manner of course not damaging for the physical integrity and the health of the patient. Such electromagnetic waves are, for example, radio waves (produced by high-frequency electrical currents) of appropriate power. For example, the frequency of the electromagnetic waves may be less than 100 MHz. In particular this frequency may be included in the band [10 kHz-100 MHz].

Such waves propagate well in air, but not as well in human tissues and even less well through the dense parts such as teeth or bones. Due to the level of electromagnetic emission, the signal received is generally fairly weak, of the order of a few microvolts ($\mu V$), and is hence fairly difficult to process.

An operational principle that nevertheless provides good results in such unfavorable conditions is the use of the relative intensity of the fields between the emission solenoids 120 to look for the point where they balance each other. Bearing in mind that the characteristics of the emitters are identical, this point corresponds to the center of the plane of the support 13 of the emission solenoids. The reception solenoid is preferably located facing the center of the sensitive surface of the image sensor 20. But this positioning is not necessary because the calculations leading to the detection or nondetection of a positioning error can very well take account of a known distance between the center of the sensitive surface of the image sensor 20 and the location of the reception solenoid.

An error distance relative to the balance of the electromagnetic fields generated by the emission solenoids can be determined from the relative intensity of the fields if the attenuation as a function of the distance is known, which may be the case either by applying the laws of electromagnetic wave propagation or by a simple calibration of the system. It is therefore possible to have a relatively precise estimation of the position of the reception solenoid relative to the plane formed by the emission solenoids using a series of triangulation calculations.

As the measurement is carried out on the amplitudes and relative phases, it is preferable for the signals emitted by each emission solenoid to have identical characteristics in terms of amplitude, frequency, phase, recurrence period and electromagnetic field created (especially polarization). The performance thereof is improved with simplified calculations. To this end, in particular, solenoids 120 that are identical to each other are provided.

It is also preferable that the emission solenoids do not all emit at the same time. Otherwise, with the information being identical in nature, it could only be more difficult to discriminate at reception (each electromagnetic signal would behave as noise towards the others). In one embodiment, the emission unit is designed to establish a control sequence for the emission solenoids based on a rule of the "one at a time" type, for example "each in turn", with which the reception unit can be synchronized. Put another way, the emission solenoids all emit, but each does so alternately. This sequence is taken into account by the processor driving the emission unit.

Detection of a Parallax Error

The embodiments described above can help in positioning the X-ray source relative to the image sensor. But correct positioning does not always suffice.

Figure 5:
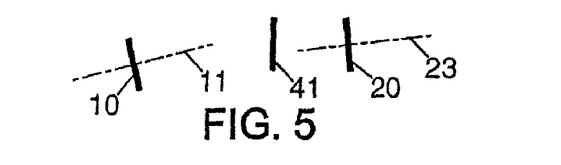
FIG. 5 is a highly simplified diagram illustrating the problem of the parallax error between the radiation source and the sensor in the context of X-ray mobile digital imaging.

With reference to FIG. 5, it is in fact additionally desirable to align the output axis 11 of the source 10 (axis of incidence of the X-rays) with the axis 23 perpendicular to the sensitive surface of the sensor 20. In the case of a lack of angular alignment (also called a parallax error) between the radiation source and the sensor, the image that is obtained of the target is distorted. This results from the directedness of the X-rays. Angular alignment is not easy to obtain in practice. The use of a mechanical positioning device, such as the sensor holder described in the introduction, allows this difficulty to be resolved. But its use suffers from the drawbacks that have already been mentioned.

Embodiments provide a solution to the additional problem of detecting a parallax error. This is because knowing the form of the electromagnetic fields also enables determination of an incident angle between the electromagnetic emitters and the electromagnetic receiver(s). This angle corresponds to the parallelism error between the planes {XG, YG} and {XC, YC} of the X-ray generator and the image sensor respectively, which corresponds to measurement of the parallax error between the first and the second plane.

It will be noted that extracting this information requires the presence of at least four emission solenoids. Put another way, in these embodiments the electromagnetic emission unit comprises at least four identical electromagnetic emitters 120.

Figure 6A:
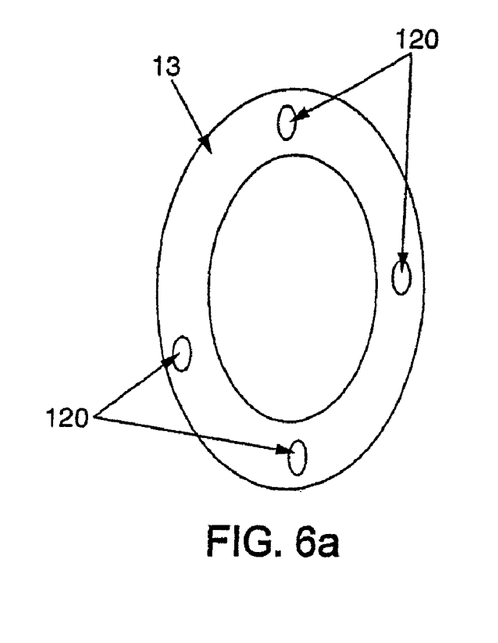
FIGS. 6a, 6b and 6c are diagrams illustrating embodiments of the electromagnetic wave emission device.

Such an embodiment is schematically represented in FIG. 6a.

The calculations enabling the incident angle between the electromagnetic emitters and the electromagnetic receiver(s) to be determined are also carried out here by the control unit 25. They employ triangulation rules and conventional trigonometry and do not need to be explained here. Indeed, the person skilled in the art will be able to implement them, for example in the form of appropriate software.

Figure 6B:
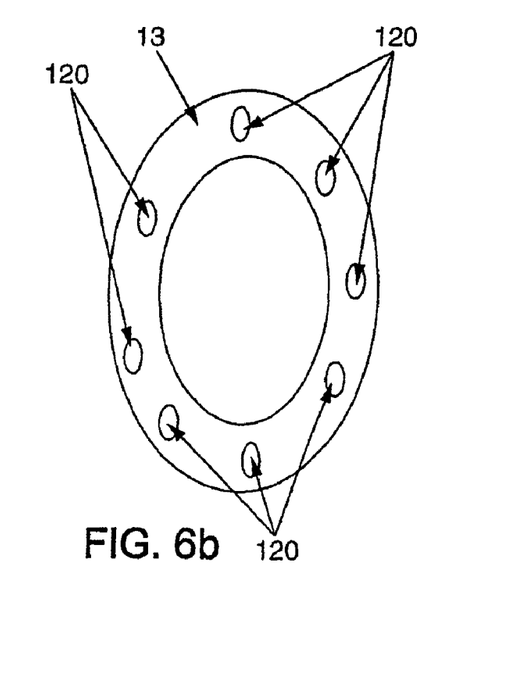

In a preferred embodiment, according to the diagram of FIG. 6b, the electromagnetic wave emission unit in fact comprises 8 identical emission solenoids or electromagnetic emitters. This number produces the best compromise between the complexity of the calculations to be carried out and the performance level attained.

Figure 6C:
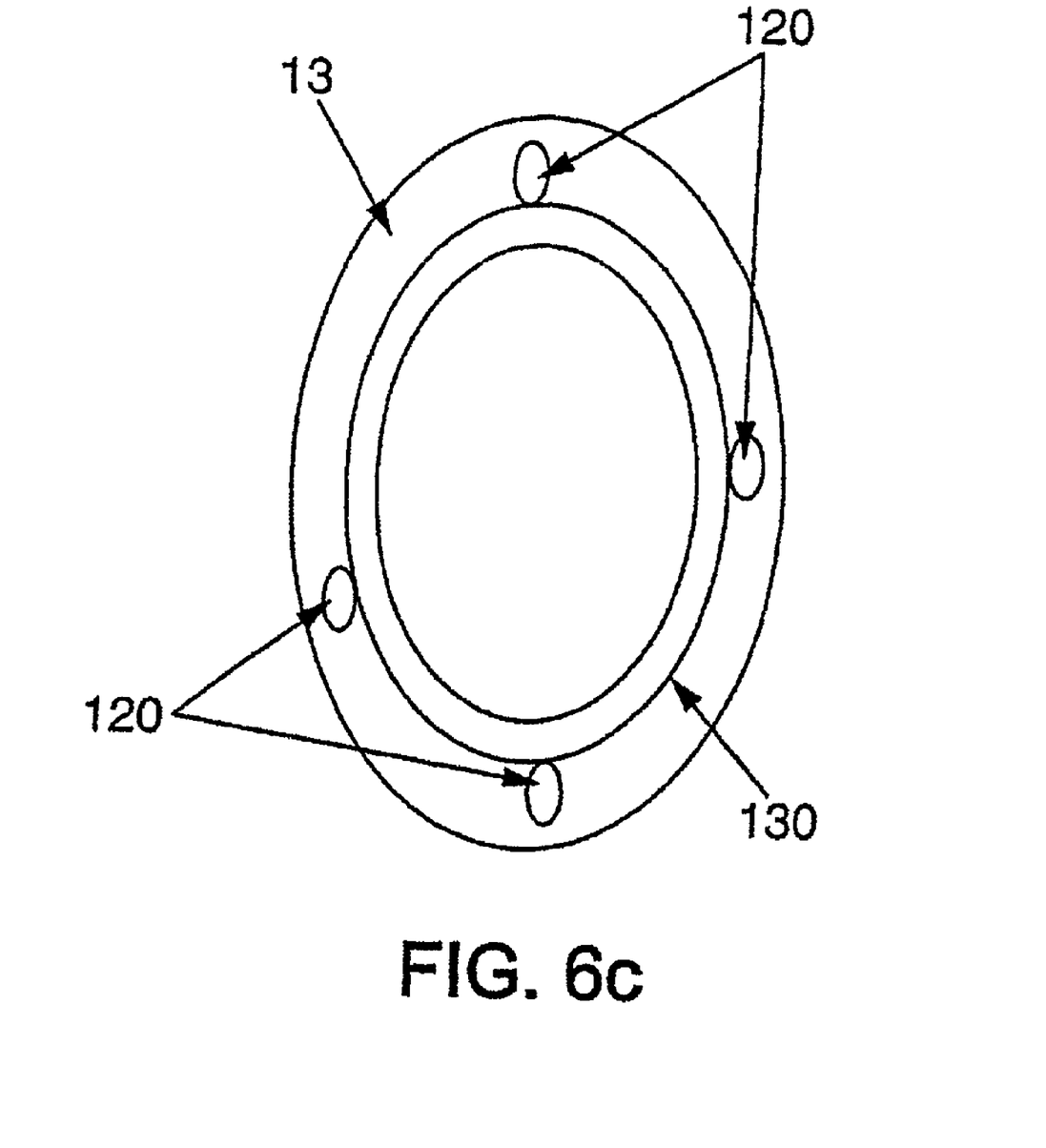

In embodiments, the N solenoids of the electromagnetic wave emission unit may include a central emission solenoid corresponding to the center of the toric support 13. Such an embodiment is, for example, illustrated in FIG. 6c, in which this central solenoid 130 has a diameter between the internal diameter and the external diameter of the torus 13. Advantageously, the solenoid 130 thus has a larger diameter, a larger surface and a higher efficiency than the solenoids 120, which enables the measurements carried out for the other solenoids to be improved.

Detection of the Orientation of the Image Sensor

When the radiological sensor is put in the mouth of the patient, the radiograph may in particular relate to the teeth of the upper jaw or of the lower jaw, from the right side or the left side of the patient. The cable connecting the control and exploitation unit 25 to the image sensor 20 requires a different angular position for this in each of these four cases. It follows from this that the orientation of the image obtained must be determined and noted on the image by the practitioner, for example by writing it on a self-adhesive patch put on the radiological negative obtained, or keyed in manually on a computer keyboard so as to appear on the negative itself.

To solve these problems and to avoid any risk of subsequent error in identifying radiological images, embodiments enable the orientation of the sensor in the mouth to be determined automatically and this to be taken account of when producing the image, so that the latter is always identified and/or presented in a corresponding manner. The device already described above, which allows determination of the position of the sensor relative to the plane of the emitter solenoids, can indeed be further improved to allow, in addition, detection of the orientation of the image sensor.

When the electromagnetic wave reception unit comprises a single reception solenoid, as in the case of the embodiment according to FIG. 4 (in which the angular position of the device is marked by a black point in a corner of the plate 23), a 180 degree rotation, for example, gives the same position. This is due to the fact that a single point corresponding to the center of the reception solenoid 230 is taken into account in the triangulation calculations.

Figure 7:
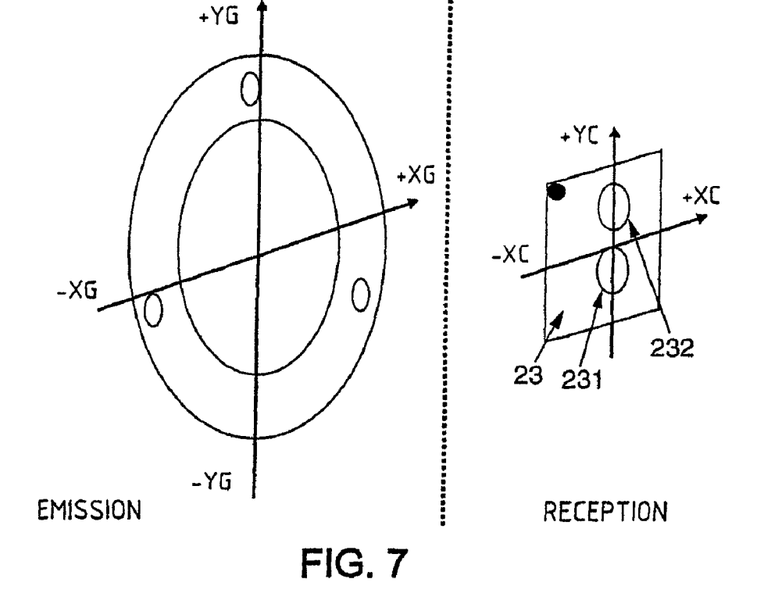
FIGS. 7, 8a and 8b are diagrams of an embodiment of an electromagnetic reception unit enabling the automatic detection of the orientation of the image sensor in its own plane.

Various angular positions of the reception unit in its own plane can be discriminated by providing at least two reception solenoids, such as the solenoids 231 and 232 from the embodiment according to FIG. 7. The electromagnetic signals coming from the electromagnetic emitters 120 of the electromagnetic emission unit are observed there at each of these solenoids. Two series of triangulation calculations are performed on the basis of the interplay of the signals respectively received at each of the receivers 231 and 232. The solenoids 231 and 232 are offset from each other relative to the reference axis or axes, which are here, for example, a vertical axis (−YC, +YC) and a horizontal axis (−XC, +XC) in the plane {XC, YC} of the image sensor.

Put another way, at least a second electromagnetic wave receiver is added to the electromagnetic wave reception unit so as to allow, when this is joined to the image sensor 20, determination of the angle formed by the axis perpendicular to the sensitive surface of the image sensor and the axis of incidence of the X-rays coming from the generator 10. These solenoids are situated in the same plane (the plane of the plate 23) and in respective positions that are nonsymmetrical relative to a first axis and/or a second axis in said plane. Determination of the position relative to the emission solenoids is then carried out for each of the reception solenoids. The relative positions then provide the angle of rotation of the plate in its own plane, which angle corresponds to the angle of rotation of the image sensor in its own plane. It is also the angle of rotation of the image sensor relative to the plane of the end of the gun 12 of the generator, the respective planes of the sensor and the generator being assumed to be parallel due to the correct parallax adjustment. Indeed, it will be noted that this method of detecting the rotation assumes that the planes {XG, YG} and {XC, YC} are parallel.

Figure 8A:
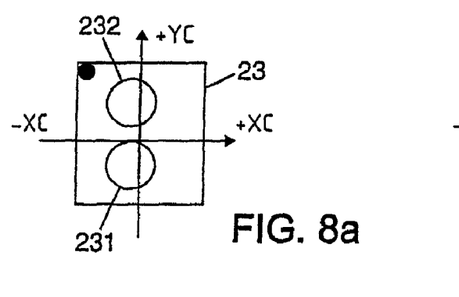
Figure 8B:
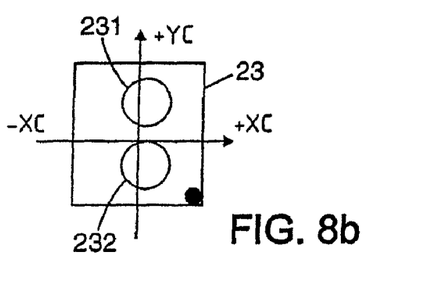

Just as the diagrams of FIGS. 8a and 8b show, in which the reception unit has been represented in two angular positions respectively offset by 180° relative to one another (as shown by the black point marking a corner of the plate 23), rotation of the plate 23 implies a difference in distance between each of the reception solenoids 231 and 232 on the one hand, and each of the emission solenoids (not visible in these figures) on the other hand.

Determination of the angular orientation of the image sensor enables automatic rotation of the image displayed on the video monitor of the facility by the applications software run on the computer 25. Of course, this also assumes that the orientation of the X-ray generator is known.

The solenoids 231 and 232 are preferably positioned a distance from each other that is as great as possible to make discrimination of the various orientations easier. In the application concerned here, this discrimination is not very difficult to attain as only four angular positions are to be discriminated (from 0 to 360 degrees in steps of 90 degrees).

Detection of the Presence of X-Rays

A digital sensor for X-ray radiology typically comprises a CCD array covered with a chemical element (corresponding to the scintillator) converting the X-rays into photons.

In facilities of the prior art, detection of the presence of X-rays (called TRIG detection) is carried out autonomously at the image sensor through the quantity of light received at the sensor exceeding a threshold. When the information about the presence of X-rays is available at the sensor, the latter is controlled in a mode called "integration" mode in which it is kept static so that it is able to detect all the X-rays that continue to flood in through to the end of the exposure period. It will be understood that detection of the presence of X-rays can be carried out only when the radiation is already active, whence there is an inevitable delay in passing into integration mode, shown in a haziness in the image. The mean delay in reaction is around 2 milliseconds for an exposure time of between 15 and 250 milliseconds.

Embodiments are also known in which the information about the presence of X-rays is provided to the sensor from the generator via a connection between the former and the latter in order to improve the image quality. But these embodiments require the functionality of each component of the facility to be taken into account from design onwards, since it necessitates an interface between a control unit of the generator and the control and exploitation unit of the image sensor. It is therefore not conceivable when these components are not foreseen from the outset as being interoperable, for example because they are provided by different manufacturers.

Figure 9:
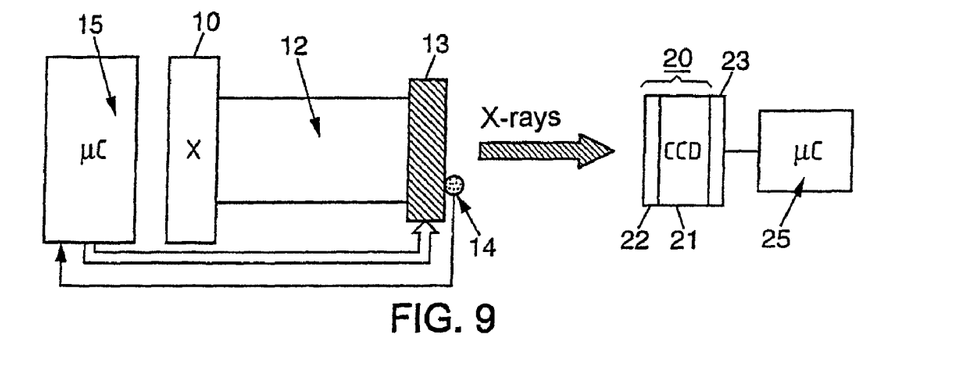
FIG. 9 is a diagram illustrating an embodiment of the facility allowing the image sensor to be put into integration mode more quickly.

To solve these problems, embodiments of the invention provide for a device for detecting X-ray radiation to be placed in front of the end of the gun 12 of the X-ray generator. This X-ray detector may advantageously be mechanically joined to the electromagnetic emission unit, for example mounted on the support 13 of the emission solenoids 120 and 130.

With reference to FIG. 9, such a detector 14, of the type with a photodiode equipped with a scintillator or another type, is for example positioned on the support 13 of the electromagnetic wave emission unit. The control unit 15 has simple electronics for conditioning the signal coming from the detector 14.

A piece of information about the presence of X-rays provided by the detector 14 is then transmitted in a coded manner by the emission solenoids 120 to the electromagnetic wave reception unit, for example in the form of a different modulation frequency. The control unit 25 of the reception unit may then control the putting of the image sensor 20 into integration mode.

The reaction time is reduced by a factor of 10 relative to detection by the image sensor itself, as the signal is very strong at the output of the gun 12, which is close to the X-ray source, and as no obstacle attenuates or obscures the radiation. In practice a reaction time of around 200 microseconds can therefore be obtained. The reduction in the delay in putting the image sensor into integration mode also allows a reduced exposure time for the same image quality.

The description of exemplary embodiments given above is not limiting, other embodiments being conceivable. For example, the CCD digital detector may be replaced by a CMOS technology detector with phototransistors (photodiodes). Likewise, the image sensor is not necessarily a digital sensor, but can also be an analogue sensor, from which the output information is or is not digitized. Finally, the radiation source is not necessarily an X-ray generator, but may also be a generator of Gamma or other radiation.

The embodiments presented above, and others, enable desynchronized operation between the emission unit and the reception unit. It is possible to profit from this property in order to create an operational device in which the emitters situated on the X-ray generator gun can operate autonomously by batteries. This avoids the use of electrical cables that are difficult to install on the generator gun which is itself installed at the end of an articulated arm of more than 2 meters.

The following other features and advantages also follow from embodiments of the invention:

- a button situated on the processing unit 15 of the emission unit may enable a voltage to be applied to the emission unit for a determined time, which may be predefined;
- the reception unit may be integrated into the radiological image sensor or on a small plate placed alongside this;
- as the digital processing employed at the electromagnetic wave reception unit requires a very high calculation power, this processing may be executed in an external base or indeed be carried out within the electronics managing the radiological image sensor, if this permits it;
- it is the electronics managing the radiological image sensor that may be responsible for managing the positioning of the generator relative to the sensor;
- the noise generated by an electromagnetic emitter does not interfere with the radiological image sensor;
- the level of emission of electromagnetic waves is compatible with EMI standards;
- the presence of the electromagnetic emitter does not exhibit incompatibility of use with an intrusive element such as a dental radiological image sensor;
- the solenoid integrated into the radiological image sensor may be the electromagnetic emitter, the solenoids joined to the generator becoming electromagnetic receivers. The basic principle remains strictly identical as the physical systems are always symmetric and reversible. The mathematical processes (triangulation calculations) are simply permuted in their principle. If these processes have to be carried out by the applications software managing the radiological image sensor (which is run on the computer for general usage by the practitioner), the reception unit operating at the X-ray generator must have a channel for communication with this applications software, either wired (USB protocol, RS232, etc.) or wireless (WIFI, Bluetooth standards, etc.); and
- the electromagnetic wave emission unit is designed to emit, and the electromagnetic wave reception unit is designed to receive, supplementary information in addition to the binary pattern. This supplementary information may comprise information about the detection of radiation from the radiation source or other control, signaling, or other information.

The invention claimed is:

1. A device for detecting incorrect positioning between a first element and a second element, comprising:

a unit for emitting electromagnetic waves suited to pass through human tissues, said unit for emitting electromagnetic waves being designed to be joined to the first element; and a unit for receiving electromagnetic waves and for digital processing designed to be joined to the second element, and cooperating with the unit for emitting electromagnetic waves to detect incorrect positioning of the first element relative to the second element, wherein the unit for emitting electromagnetic waves comprises a number N of electromagnetic emitters positioned in approximately the same plane, where N is an integer greater than or equal to 3, and a control unit configured to have each of these N electromagnetic emitters emit a respective electromagnetic signal, said electromagnetic signal corresponding to a modulated directional electromagnetic field according to a frame having a binary pattern specific to said emitter and enabling the unit for reception of electromagnetic waves to identify the electromagnetic signals coming respectively from each of the electromagnetic emitters by signal processing.

2. The device as claimed in claim 1, wherein the electromagnetic unit for receiving electromagnetic waves comprises at least one reception solenoid.

3. The device as claimed in claim 2, wherein the unit for receiving electromagnetic waves is configured to obtain an estimation of the position of the reception solenoid relative to the plane formed by the electromagnetic emitters by using a series of triangulation calculations.

4. The device as claimed in claim 3, wherein the control unit of the unit for emitting electromagnetic waves is configured in such a way that the electromagnetic emitters emit one at a time, each with a given recurrence period.

5. The device as claimed in claim 4, wherein the control unit of the unit for emitting electromagnetic waves is configured in such a way that the signals emitted by the electromagnetic emitters have, apart from the effect of modulation, common characteristics in terms of amplitude, frequency, phase, recurrence period and electromagnetic field.

6. The device as claimed in claim 3, wherein N is at least equal to 4.

7. The device as claimed in claim 3, wherein N is equal to 8.

8. The device as claimed in claim 3, wherein the N electromagnetic emitters are positioned equidistantly in a plane perpendicular to an incident direction of emission from the radiation source.

9. The device as claimed in claim 3, wherein the N electromagnetic emitters each comprise a solenoid.

10. The device as claimed in claim 8, wherein the solenoids are arranged on a toric support, one of the solenoids having a center corresponding to the center of the support and a diameter between the internal diameter and the external diameter of the support.

11. The device as claimed in claim 6, wherein the unit for receiving electromagnetic waves is configured, in addition, to determine by signal processing an angle between a plane of the unit for emitting electromagnetic waves and a plane of the unit fore receiving electromagnetic waves.

12. The device as claimed in claim 3, wherein the unit for receiving electromagnetic waves comprises a number M of electromagnetic receivers located in the same plane and in respective positions that are nonsymmetrical relative to a first axis and/or a second axis in said plane, where M is an integer greater than or equal to 2, and in which the unit for receiving electromagnetic waves is configured, in addition, to determine by signal processing the signals coming from the various electromagnetic emitters for each of the M electromagnetic receivers and to deduce from this a rotation of said plane relative to said first axis and/or said second axis respectively.

13. The device as claimed in claim 3, wherein the unit for emitting electromagnetic waves is designed to emit, and the unit for receiving electromagnetic waves is designed to receive, supplementary information in addition to the binary pattern.

14. The device as claimed in claim 13, wherein the electromagnetic waves are radio waves.

15. The device as claimed in claim 14, wherein the frequency of the electromagnetic waves is less than 100 MHz.

16. A mobile imaging facility comprising:
a radiation source; and
an image sensor, having a surface sensitive to the radiation generated by the radiation source and not joined to the radiation source, characterized in that it further comprises a device for detecting incorrect positioning between a first element and a second element, the device comprising:
a unit for emitting electromagnetic waves suited to pass through human tissues, said for emitting electromagnetic waves unit being designed to be joined to the first element; and
a unit for receiving electromagnetic waves and for digital processing designed to be joined to the second element, and cooperating with the unit for emitting electromagnetic waves to detect incorrect positioning of the first element relative to the second element,
wherein the unit for emitting electromagnetic waves comprises a number N of electromagnetic emitters positioned in approximately the same plane, where N is an integer greater than or equal to 3, and a control unit configured to have each of these N electromagnetic emitters emit a respective electromagnetic signal, said electromagnetic signal corresponding to a modulated directional electromagnetic field according to a frame having a binary pattern specific to said emitter and enabling the unit for reception of electromagnetic waves to identify the electromagnetic signals coming respectively from each of the electromagnetic emitters by signal processing;
the unit for emitting electromagnetic waves is joined to the radiation source; and
the unit for receiving electromagnetic waves and for digital processing is joined to the image sensor.

17. The mobile imaging facility as claimed in claim 16, further comprising a device for detecting the radiation generated by the radiation source, joined to the unit for emitting electromagnetic waves, wherein the unit for emitting electromagnetic waves is designed to transmit a piece of information about the presence of radiation provided by the radiation detector to the unit for receiving electromagnetic waves.

18. A mobile imaging facility comprising:
a radiation source; and
an image sensor, having a surface sensitive to the radiation generated by the radiation source and not joined to the radiation source, characterized in that it further comprises a device for detecting incorrect positioning between a first element and a second element, the device comprising:
a unit for emitting electromagnetic waves suited to pass through human tissues, said unit for emitting electromagnetic waves being designed to be joined to the first element; and
a unit for receiving electromagnetic waves and for digital processing designed to be joined to the second element, and cooperating with the unit for emitting electromagnetic waves to detect incorrect positioning of the first element relative to the second element,
wherein the unit for emitting electromagnetic waves comprises a number N of electromagnetic emitters positioned in approximately the same plane, where N is an integer greater than or equal to 3, and a control unit configured to have each of these N electromagnetic emitters emit a respective electromagnetic signal, said electromagnetic signal corresponding to a modulated directional electromagnetic field according to a frame having a binary pattern specific to said emitter and enabling the unit for reception of electromagnetic waves to identify the electromagnetic signals coming respectively from each of the electromagnetic emitters by signal processing;
the unit for emitting electromagnetic waves is joined to the image sensor; and
the unit for receiving electromagnetic waves and for digital processing is joined to the radiation source.

19. The mobile imaging facility as claimed in claim 18, further comprising a device for detecting the radiation generated by the radiation source, joined to the unit for emitting electromagnetic waves, wherein the unit for emitting electromagnetic waves is designed to transmit a piece of information about the presence of radiation provided by the radiation detector to the unit for receiving electromagnetic waves.

* * * * *